United States Patent [19]
Johnson et al.

[11] Patent Number: 5,258,026
[45] Date of Patent: Nov. 2, 1993

[54] ENDOSCOPIC AUGMENTATION MAMMOPLASTY AND INSTRUMENTS THEREFOR

[76] Inventors: Gerald W. Johnson, 2010 Castle Rock, Houston, Tex. 77090; Jeffrey W. Johnson, 2112 S. L St., Ft. Smith, Ark. 72901

[21] Appl. No.: 832,072

[22] Filed: Feb. 6, 1992

[51] Int. Cl.$^5$ ............................................. A61F 2/12
[52] U.S. Cl. ........................................ 623/8; 128/898
[58] Field of Search ................... 623/8, 7, 66; 128/4, 128/6, 898

[56] References Cited

U.S. PATENT DOCUMENTS

| | | | |
|---|---|---|---|
| 2,516,628 | 7/1950 | Held | 128/4 |
| 3,834,392 | 9/1974 | Lampman et al. | 128/4 |
| 4,470,160 | 9/1984 | Cavon | 623/8 |
| 4,643,733 | 2/1987 | Becker | 623/8 |
| 4,908,029 | 3/1990 | Bark et al. | 623/8 |
| 4,969,899 | 11/1990 | Cox | 623/8 |
| 5,029,573 | 7/1991 | Chow | 128/4 |
| 5,050,585 | 9/1991 | Takahashi | 128/4 |
| 5,125,910 | 6/1992 | Freitas | 128/4 |
| 5,176,649 | 1/1993 | Wakabayashi | 604/264 |

Primary Examiner—Randall L. Green
Assistant Examiner—Gina M. Gualtieri
Attorney, Agent, or Firm—Neal J. Mosely

[57] ABSTRACT

A surgical procedure for breast augmentation is disclosed in which an incision is made inside the navel or umbilicus. An endotube which has an obturator with a bullet shaped tip is introduced into this incision and pushed from the umbilicus, staying just above the fascia of the interior abdominal and chest wall, and below the subcutaneous tissue and fat, to a position behind the breast. The obturator is removed and an endoscope used to verify the proper location of the tunnel. The endotube is removed leaving a temporary tunnel leading to a space behind the breast. A hollow prosthesis is rolled up tightly, positioned inside the end of the endotube and pushed into the tunnel behind the breast. The prosthesis is held in place by the hand of the surgeon on the breast and the endotube removed. The prosthesis is pumped full of saline solution to about a 50% overfill. The filling of the prosthesis with saline solution, together with the manipulation and pressure by the surgeon causes the tissues behind the breast to be dissected to form a pocket filled by the implant. After a short time, excess liquid is allowed to flow out of the prosthesis and the fill tube removed. The procedure is then repeated for the other breast. The navel is sutured and the patient may then go home from the recovery room. Special electrosurgical and electrocauterizing instruments are provided.

20 Claims, 5 Drawing Sheets

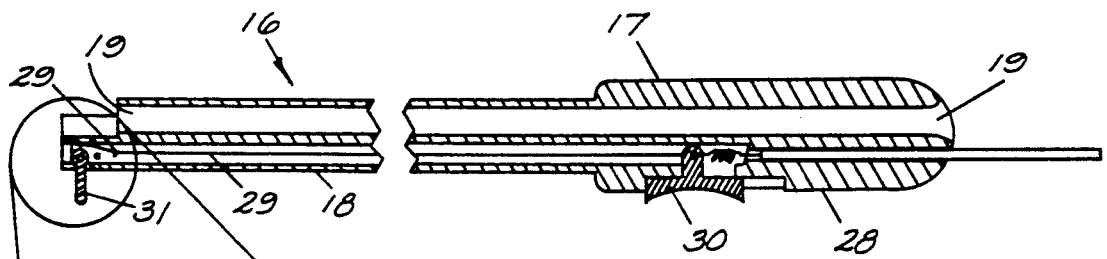
FIGURE 5
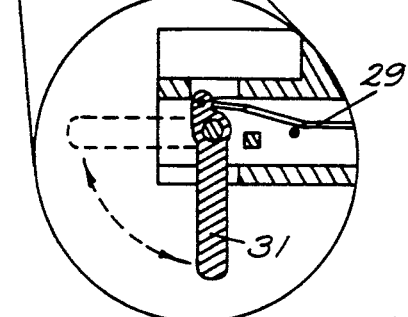
FIGURE 5A
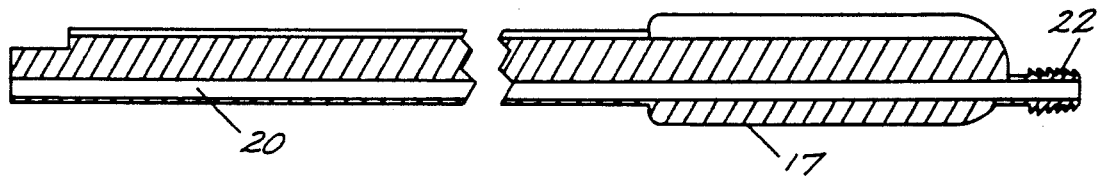
FIGURE 6
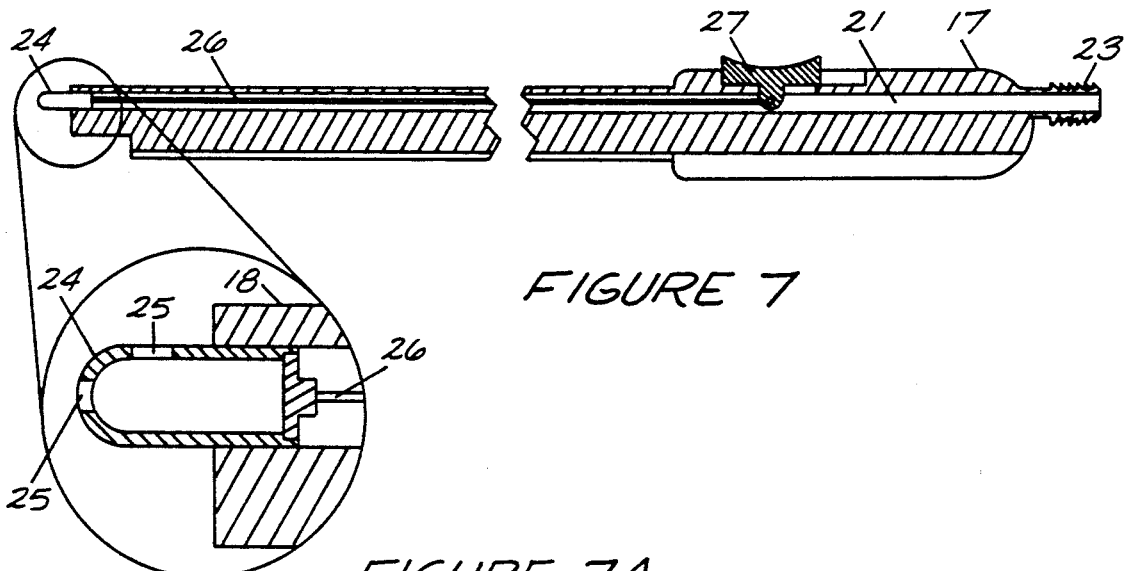
FIGURE 7
FIGURE 7A

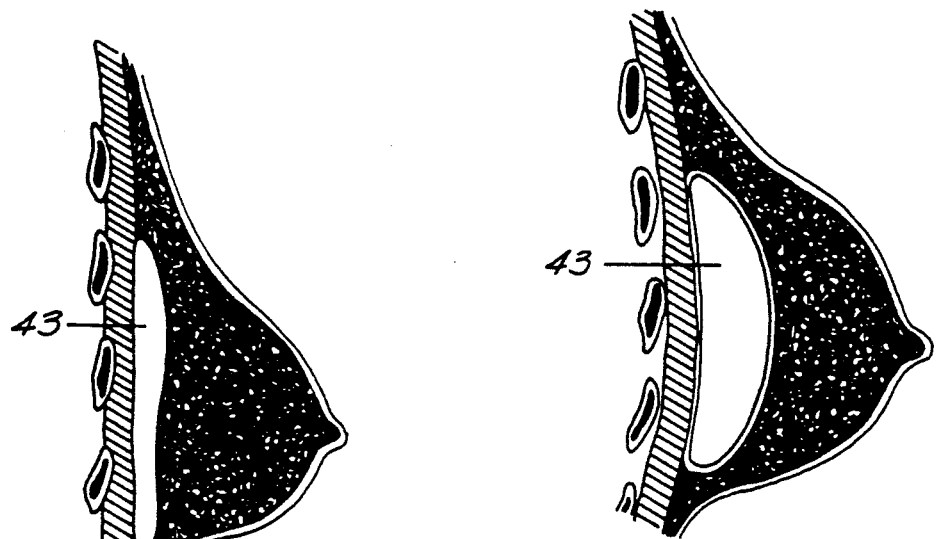
FIGURE 15
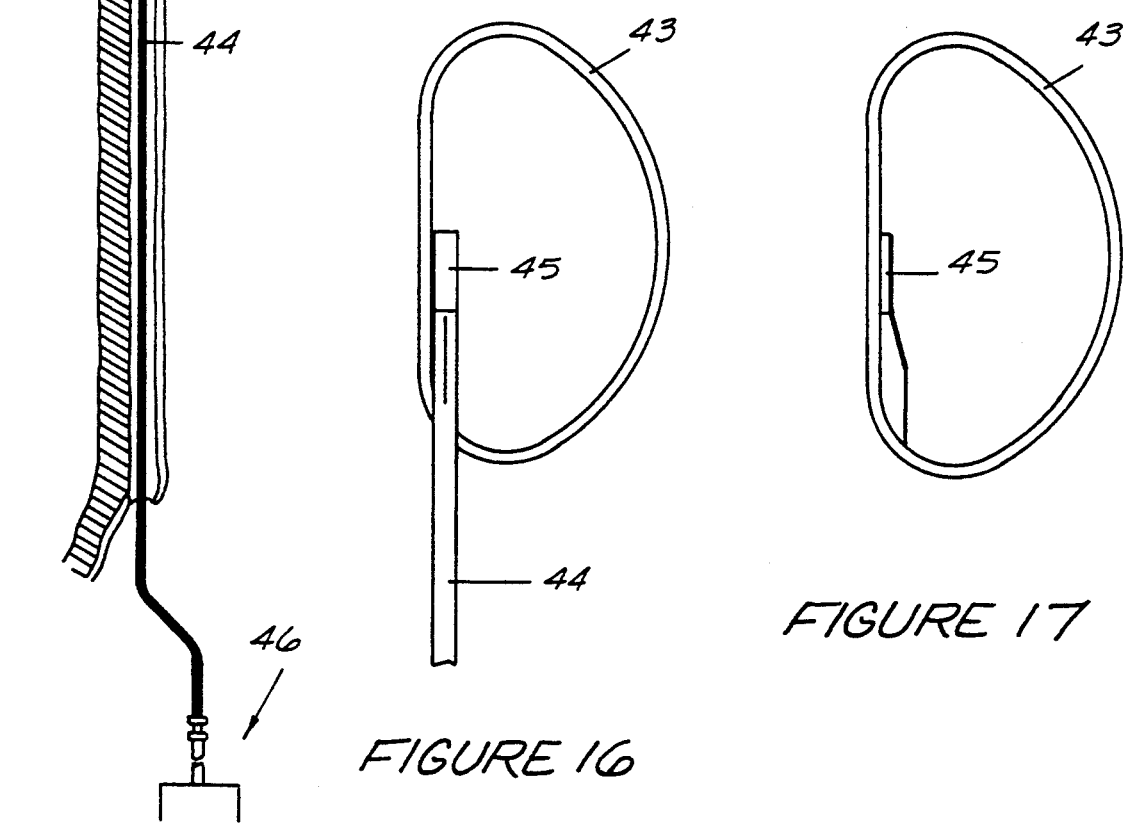
FIGURE 17
FIGURE 16
FIGURE 14

ENDOSCOPIC AUGMENTATION MAMMOPLASTY AND INSTRUMENTS THEREFOR

BACKGROUND OF THE INVENTION

1. Field of the Invention

This invention relates to new and useful improvements in breast augmentation mammoplasty and more particularly to an endoscopic approach to the operation. The invention relates generally to a surgical apparatus and technique utilizing an endotube and obturator, special instruments, and the insertion of a breast prosthesis through a tunnel from the navel to a space behind the breast which is expanded by the prosthesis into a pocket in which it is confined.

2. Brief Description of the Prior Art

Historically, material such as paraffin, glass beads, silicone gel and a patient's own fat have been used by injection means to augment or enhance the female breast. These methods have been abandoned.

Current methods of enhancement involve such diverse means as using a flap of the patient's own tissue (skin and subcutaneous fat plus the underlying fascia and/or muscle and fascia) taken from another location on the body and transferred to the breast by microvascular anastomosis—called a free flap transfer, or transferred to the breast still attached to the muscle and fascia, with one end of the muscle remaining attached to its blood supply (which in turn keeps the skin and fat attached to it alive)—called a myocutaneous flap or a tram flap.

These methods of transfer of flaps of the patient's own tissue, however, are seldom if ever used for the cosmetic enlargement of the female breast. These methods are almost always used for reconstruction of the female breast after cancer surgery or other post surgical complications.

Current methods of enhancement for purely cosmetic purposes involve the placement of an implant device beneath each breast or beneath each pectoralis major muscle (which places the implant device beneath both the breast and its underlying pectoralis major muscle).

Historically, every method or surgical means for implantation of a device for breast enlargement involves the making of an incision on each breast (usually in the nipple area or inframammary crease area) or making an incision in each axillary area and surgically creating a pocket (or space) underneath each breast or underneath each breast and pectoralis muscle. Beneath the breast only is called subglandular and beneath the breast and muscle is called submuscular—also called submammary and submusculofacia.

In an occasional patient who had an existing scar in the midline chest or upper abdomen or who was undergoing an abdommoplasty (tummy tuck), a surgical approach was made to each breast, using that one incision and the pockets created to contain the implant devices.

In all the medical literature, surgical creation of the pocket, in the subglandular or in the submuscular location, involves two basic techniques, each technique utilizing two skin incisions (nipple, inframammary or axillary) one incision to gain access to each breast to create the pockets. The two techniques are the blunt dissection and the sharp dissection technique.

The blunt dissection technique involves gaining access to the breast through a skin incision. The surgeon then identifies the location (subglandular or submuscular) and, using a finger or other blunt surgical instrument, the breast is bluntly separated from the pectoralis muscle fascia (to create the subglandular pocket) or the pectoralis major muscle is bluntly separated from the chest wall (to create the submuscular pocket). The blunt dissection technique is usually done "blindly" not under direct vision.

The sharp dissection technique involves gaining access to the breast through a skin incision. The surgeon then uses a knife, scissors, electrocautery, or laser to dissect the subglandular or submuscular pocket. The sharp dissection technique is almost always done under direct vision.

The blunt dissection technique generally causes more bleeding and bruising, and after blunt dissection many surgeons will then use direct vision and cautery or laser to control any blood vessels that are bleeding.

Many surgeons will also use a combinations of the blunt dissection and sharp dissection techniques to create the pocket for the implant devices.

One of the major references describing breast surgery is AESTHETIC AND RECONSTRUCTIVE BREAST SURGERY, John Bostwick III, M.D., The C.V. Mosby Company 1983 which is extracted below to describe conventional methods in breast surgery. The reference is thoroughly illustrated for ease in following the text.

Innervation—Sensory nerves to the breast enter from the third to the sixth lateral intercostal nerves. These nerves pass through the interdigitations of the serratus anterior muscle. The second intercostal nerve, the intercostobrachial, goes across the axilla to the upper medial arm. It is usually divided during a mastectomy, resulting in anesthesia and paresthesia of the upper medial arm. It can also be damaged during axillary augmentation mammaplasty. Painful neuromas can occur when the lateral cutaneous nerves have been divided over the serratus anterior muscle during mastectomy. Resection of these neuromas and coverage with an implant or flap can give helpful improvement for these symptoms.

The upper portion of the breast and the infraclavicular skin are supplied by supraclavicular branches from the cervical plexus, which extend downward beneath the platysma muscle. This upper cervical plexus innervation should be remembered when a local block of the breast is performed. Anterior intercostal segmental nerves supply the medial breast and presternal area and enter with the internal thoracic perforators.

Innervation of the nipple-areola is primarily the fourth lateral intercostal branch. It enters laterally through the fourth interspace and runs medially under the deep fascia for a few centimeters. It then courses upward through the breast tissue to supply the nipple-areola. The third and fifth lateral nerves as well as the third through the fifth anterior intercostal nerves provide some sensation for the nipple-areola.

Lymphatics—The lymphatics of the breast originate throughout the gland about the lobules and the lactiferous ducts and communicate with the periarcolar lymphatic plexus. There are also direct lymphatic connections through the deep fascia into the underlying muscles. Primary lymph efferents pass from the upper outer quadrant of the breast, around the pectoralis major muscle, to the pectoral group of nodes. Some also pass directly to the subscapular nodes. The lymph then drains to the central nodes and next to the apical nodes of the axilla. The medial lymph channels accompany the internal thoracic perforators and drain to the parasternal nodes. These medial lymph nodes receive some lymph from the entire gland.

Placement of incisions—The primary consideration for breast augmentation is enlargement of the breasts to a size, contour, and form that is symmetrical and acceptable to the patient. Most patients are not concerned with incisions when the erythema fades, particularly if the breasts are soft and attractive. Selection of incision location must be individualized. Three incisions often used for breast augmentation are the inframammary, periareolar, and axillary.

Implant position—Implant position is a key factor in obtaining an excellent result from augmentation mammaplasty. When operations for breast enlargement were first developed, implants were placed over the chest wall musculature. This seemed to be the natural position to enlarge breast size. With this retromammary position there was and continues to be a high incidence of capsular contracture around the implant. This condition has developed despite the use of different implants, varied incisions, larger pockets, intraoperative antibiotics, and postoperative massage.

Placement of an implant in the submusculofascial position has resulted in a higher incidence of acceptably soft breasts for my patients. The implant is beneath the pectoralis major muscle and portions of the serratus anterior, rectus abdominis, and external oblique fascia. The submusculorascial implant position gives an attractive augmentation and does not cause functional impairment.

This inframammary approach gives direct access to the submusculofascial position for breast augmentation. There is minimal disturbance of breast tissue with this approach.

Surgical approach and techniques—Accurate preoperative markings are an essential part of any breast operation. The patient should be upright when the drawings are made. The extent of the undermining for the pocket is marked above, usually to the second rib, laterally to the midaxillary line, and medically to the medial extent of the pectoralis major origins but not to the midline.

The inframammary crease dissection line is determined. If the breast is quite small and the distance from the lower areola to the inframammary crease is less than 5 cm, the inframammary crease must be lowered to 5 to 6 cm below the areola and the pocket dissected downward. If the inframammary crease is positioned properly, the pocket goes 1 cm below this crease.

A blunt subpectoral dissector or large urethral sound (size 26 French) is used to detach the pectoral muscle bluntly from the sternum and from its lower costal origins. It is essential that the lower pectoralis major fibers be divided and a pocket created sufficiently low beneath the musculofascial layer; otherwise the implant position will be too high.

It is more difficult to create a symmetrical pocket from the axillary approach. Time spent achieving symmetry is essential. Most postoperative disappointments following this approach result from failure to create a low enough pocket and failure to develop symmetrical pockets.

Submammary augmentation—When the submammary implant position is chosen, the same periareolar, inframammary, or axillary incisions can be used to approach the retromammary space. The markings are the same as for submusculofascial breast augmentation. Elevation of the breast then proceeds above the musculofascial layer with primarily blunt dissection. Hemostasis in this plane between the superficial and deep fascia must be exacting. Fiber optic lights and a headlight are helpful. In the author's experience, hematomas occur more frequently with submammary augmentation than with the submuscular approach.

The pocket is irrigated to remove all loose material such as clots or fatty globules. Preplaced sutures are used before implant positioning. A retromammary pocket is developed through an inframammary incision. After adequate hemastasis is ensured, the silicone breast implant is inserted. Preplaced sutures are helpful to protect the implant from damage by a needle.

Periareolar approach—A periareolar incision is made, and the superficial dissection is made toward the inframammary crease. The breast parenchyma is retracted superiorly, and the retromammary pocket is dissected over the deep fascia. The silicone breast implant is then positioned in the submammary pocket, and the wound is closed in layers.

The periareolar approach gives adequate access for submusculofascial dissection. However, some breast tissue must be divided with this technique. The line of incision requires minimal disturbance of breast tissue.

Objections to breast surgery—For some time, there have been objections raised to cosmetic breast surgery for a variety of reason. One such objection is that the scars from the operation are difficult to hide and the augmentation of the breast is sometimes accompanied by undesired scar tissue. In addition, the FDA has recently placed a temporary hold on the marketing of silicone filled breast implants because of doubts about their safety. Consequently, there has been a need for safer implants and an even greater need for a surgical procedure which minimizes or conceals scarring.

A number of U.S. patents illustrate the state of the art on instruments used in endoscopic surgery:

Wappler U.S. Pat. No. 1,880,551 shows a surgical endoscope.

Yoon U.S. Pat. No. 4,254,762 shows a safety surgical endoscope.

Santangelo U.S. Pat. No. 4,610,242 shows a surgical endoscope and surgical knife therein.

Storz U.S. Pat. No. 4,656,999 shows a surgical endoscope with surgical blade moved by a scissors type operator.

Nicholson U.S. Pat. No. 4,497,320 describes a cutting surgical knife for arthroscopic surgery.

Lichtman U.S. Pat. No. Des. 286,438 shows a design for a surgical obturator.

SUMMARY OF THE INVENTION

One of the objects of this invention is to provide a new and improved assembly of surgical instruments for use in endoscopic breast augmentation mammoplasty.

Another object of this invention to provide a new and improved obturator and endotube for opening a tunnel and for introduction of surgical instruments in endoscopic breast augmentation mammoplasty.

Another object of this invention to provide a new and improved electrosurgical instrument for observing endoscopic breast augmentation mammoplasty.

Another object of this invention is to provide a new and improved dissector for use in endoscopic breast augmentation mammoplasty.

Another object of this invention is to provide a new and improved endoscope for use in endoscopic breast augmentation mammoplasty.

Another object of this invention is to provide a new and improved surgical procedure comprising an endoscopic breast augmentation mammoplasty.

Another object of this invention is to provide a new and improved procedure for breast augmentation surgery which utilizes only one incision to operate on both breasts.

Another object of this invention is to provide a new and improved procedure for breast augmentation surgery in which the resultant scar is not on the breasts or in the axillary (arm pit) area, and is virtually invisible down inside the umbilicus.

Another object of this invention is to provide a new and improved procedure for breast augmentation surgery in which there is minimal bleeding, bruising and swelling as a result of the "tissue expansion" technique to dissect the pocket, as opposed to the sharp and/or blunt techniques of dissection presently used.

Another object of this invention is to provide a new and improved procedure for breast augmentation surgery in which there is much less damage to nerves than caused by other techniques currently used.

Another object of this invention is to provide a new and improved surgical procedure comprising an endoscopic breast augmentation mammoplasty which reduces postoperative pain and virtually eliminates visible scarring.

Another object of this invention is to provide a new and improved breast augmentation surgical procedure and instruments which permit the direct, undistorted visualization of the site during the operation.

Still another object of this invention is to provide an endoscopic breast augmentation mammoplasty performed through an incision within the navel which virtually eliminates visable scarring.

Still another object of this invention is to provide an endoscopic breast augmentation mammoplasty wherein an incision is made through the navel and an endotube and obturator are forced between the skin and the fascia to form a tunnel, the obturator is removed and an endoscope inserted through the endotube to observe the location of the submammary tunnel thus formed.

Still another object of this invention is to provide an endoscopic breast augmentation mammoplasty wherein an incision is made through the navel and an endotube and obturator are forced between the skin and the fascia to form a tunnel, the obturator and endotube are removed and a hollow breast prosthesis rolled tightly and the tube and prosthesis inserted through the tunnel to place the prosthesis in the end of the tunnel behind the breast; and the prosthesis is then filled with saline solution through a fill tube which is subsequently removed.

Still another object of this invention is to provide an endoscopic breast augmentation mammoplasty wherein an incision is made through the navel and an endotube and obturator are forced between the skin and the fascia to form a tunnel, the obturator and endotube are removed and a hollow breast prosthesis rolled tightly and the tube and prosthesis inserted through the tunnel to place the prosthesis in the end of the tunnel behind the breast; and the prosthesis is then overfilled by about 50% with saline solution through a fill tube thereby creating a subglandular pocket t contain the prosthesis without the need for sharp or blunt dissection which results in less surgical trauma, less bleeding and less chance for nerve damage. The excess liquid is subsequently removed thereby leaving the necessary extra room in the pocket to allow the prosthesis mobility so the augmented breast feels soft and natural. The fill tube is then removed from the prosthesis.

Other objects of the invention will become apparent from time to time throughout the specification and claims as hereinafter related.

These objects and other objects of the invention are accomplished by a novel surgical procedure for augmentation of the female breast. The method is one where an incision is made inside the navel or umbilicus. An endotube which has an obturator with a bullet shaped tip is introduced into this incision and is pushed from the umbilicus, staying just above the fascia of the interior abdominal and chest wall, and below the subcutaneous tissue and fat, to a position behind the breast. A tunnel is made behind the breast to receive an implant. The obturator is removed and an endoscope is used to verify the proper location of the tunnel. The endotube is removed leaving a temporary tunnel leading to a space behind the breast. A hollow prosthesis is rolled up tightly, positioned inside the end of the endotube and pushed into the tunnel to its position behind the breast. The prosthesis is held in place by the hand of the surgeon on the breast and the endotube removed. The prosthesis is then pumped full of saline solution to about a 50% overfill. The filling of the prosthesis with saline solution, together with the manipulation and pressure by the surgeon causes the tissues behind the breast to be dissected to form a pocket filled by the implant. After a short time, the excess liquid is allowed to flow out of the prosthesis and the fill tube removed. The procedure is then repeated for the other breast. The navel is sutured and the patient may then go directly home from the recovery room with no hospitalization required. Special electrosurgical and electrocauterizing instruments are provided.

BRIEF DESCRIPTION OF THE DRAWINGS

FIG. 5 is a sectional view taken on the section lines 5—5 of FIG. 4 showing the electrosurgical and electrocauterizing and endoscopic viewing portions of the instrument.

FIG. 5A is a detail view, slightly enlarged, of the electrosurgical or electrocauterizing head of the instrument.

FIG. 6 is a sectional view taken on the section lines 6—6 of FIG. 4 showing the irrigation portion of the instrument.

FIG. 7 is a sectional view taken on the section lines 7—7 of FIG. 4 showing the suction portion of the instrument.

FIG. 7A is a detail view, slightly enlarged, of the adjustable suction tip on the instrument.

FIG. 14 is a sectional view of a female torso, including the rib cage and the breast, as in FIG. 13, showing the endotube removed and a breast prosthesis inserted beneath the breast in the pocket formed in a previous step in the procedure and showing the prosthesis fill tube connected to a pump for filling the prosthesis.

FIG. 15 is a sectional view on the female breast showing the prosthesis filled and in place.

FIG. 16 is a sectional view of the breast prosthesis with a fill tube in place for filling.

FIG. 17 is a sectional view of the breast prosthesis with the fill tube removed and the fill valve closed after filling.

DESCRIPTION OF THE PREFERRED EMBODIMENTS THE SURGICAL INSTRUMENTS

Figure 1:
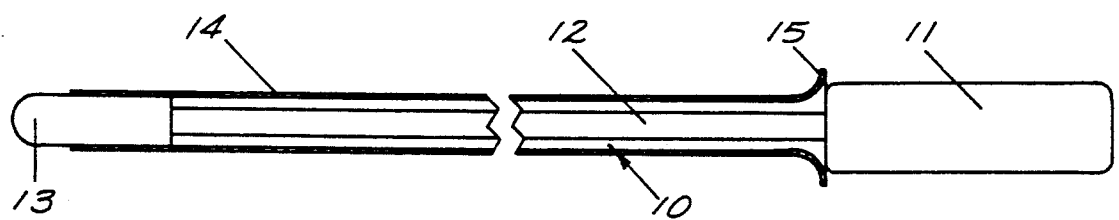
FIG. 1 is a view, partly in section, of an endotube and obturator for use in an endoscopic breast augmentation mammoplasty according to a preferred embodiment of this invention.
Figure 2:
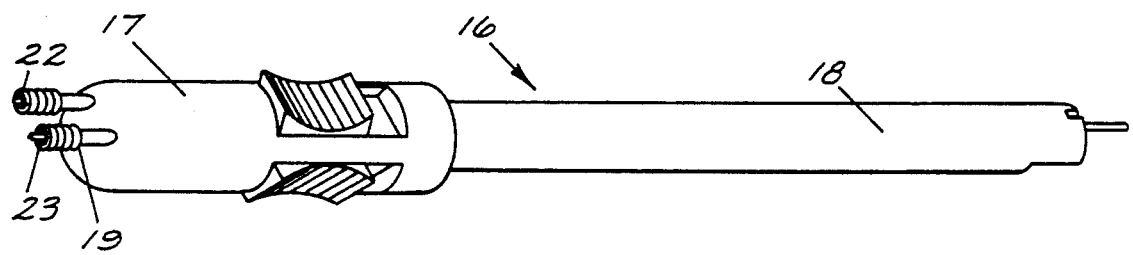
FIG. 2 is an isometric view from one end of an electrosurgical instrument, for insertion through the endotube shown in FIG. 1, having provision for electrosurgery or electrocauterization, irrigation and vacuum, and endoscopic viewing according to a preferred embodiment of this invention.
Figure 3:
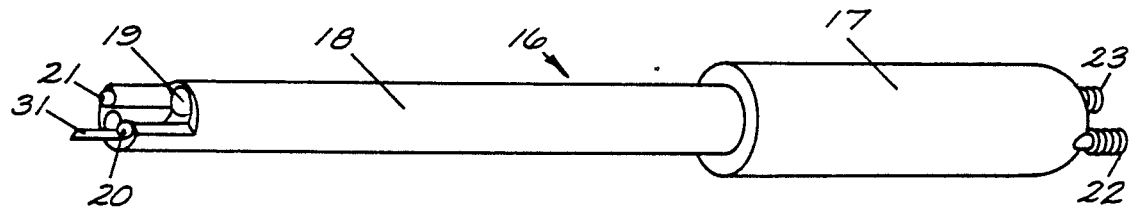
FIG. 3 is an isometric view from the other end of the electrosurgical instrument shown in FIG. 2, for insertion through the endotube shown in FIG. 1, having provision for electrosurgery or electrocauterization, irrigation and vacuum, and endoscopic viewing according to a preferred embodiment of this invention.
Figure 4:
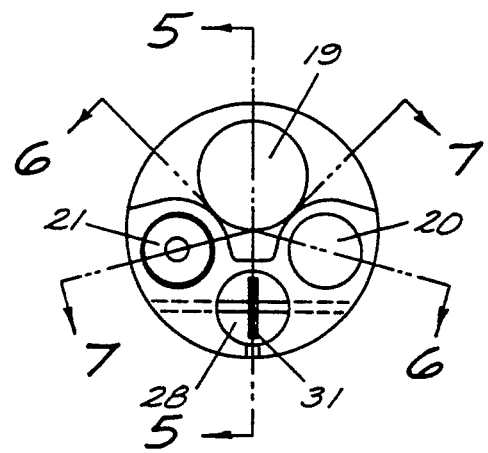
FIG. 4 is an end elevation from the left end of the instrument as shown in FIG. 3.

Referring to the drawings by numerals of reference, and more particularly to FIGS. 1-8, there are shown the improved surgical instruments forming a preferred embodiment of this invention and used in the method of endoscopic breast augmentation mammoplasty as described hereinafter. In the description of these instruments, the materials of construction and dimensions are somewhat critical for obtaining the desired results in breast augmentation surgery.

An obturator 10 (FIG. 1) comprises a handle 11, rod 12, and bullet shaped nose piece 13, preferably formed of surgical stainless steel or plastic of satisfactory strength. The obturator (or trocar) is shown in position fully inserted inside a hollow endotube 14 which is open at both ends and has a flared end portion 15 adjacent to handle 11. Both the endotube 14 and obturator 10 are preferably formed of surgical grade stainless or plastic of satisfactory strength steel. While surgical steel is preferred for instruments having long life, it may be desirable to make the instruments of a sterile plastic which may be disposed of after each operation.

The obturator 10 is about 24" long including the handle 11 and the bullet shaped nose piece 13 is sized for a sliding fit inside endotube 14. The endotube 14 is about 16" long, having an I.D. of 0.70" and O.D. of 0.73". Smaller sizes may be used if desired. When the obturator 10 is assembled in the endotube 14, the distance from the flared end 15 to the end of bullet-shaped nose piece 13 is about 18".

The dimensions are chosen to fit the requirements of the surgery. The length required is sufficient to extend from the navel to a point behind the breast of the surgical patient. Different lengths may be required for different sizes of patients. The diameter of the endotube 14 and obturator 10 are chosen to provide an opening large enough for the surgical instruments which are to be introduced through the endotube 14 without being so large that excessive trauma is produced by the surgical procedure.

In FIGS. 2-7A, there is shown a combined instrument for irrigation, application of vacuum, electrocutting and electrocauterization, or fiber optic laser operation, and endoscopic viewing. The electrosurgical instrument 16 (FIGS. 2 and 3), preferably formed of surgical stainless steel or a hard plastic such as polyurethane or polycarbonate, comprises a handle 17 and body portion 18. The instrument 16 is of sufficient length to extend through and out of the end of endotube 14 during use and body portion 18 has a diameter permitting a sliding fit therein.

Instrument 16 has a longitudinal passage 19 (FIGS. 2-5) for receiving an endoscope during use to observe the site of the surgery. Instrument 16 also has passages 20 (FIG. 6) and 21 (FIG. 7) for irrigation and suction. These passages may be combined into a single passage, if desired. Passage 20 has an inlet fitting 22 for connection to an irrigation tube. Passage 21 has an inlet fitting 23 for connection to vacuum for suctioning the surgical site. A hollow suction tip 24, with apertures 25, is positioned in the outlet end of passage 21 and slidable therein for longitudinal extension and retraction by an operating rod 25 movable by actuating lever 26 pivoted in handle 17.

Instrument 16 has a longitudinal passage 28 in which there is positioned a blade electrode 31 for electrocutting or cauterization. An electrode actuating lever 30 on handle 17 is connected remote linkage 29 (of hard conductive steel) to extend or retract blade 31. The distal end of linkage 29 has a movable blade tip 31 pivoted thereon. Extension and retraction of blade linkage 29 by lever 30 is operable to pivot tip 31 inwardly and outwardly to permit cutting and cauterization in an area defined by a circle having the radius of cutting tip 31. Instrument 16 may have a laser cutting and cauterizing element (same as 31) substituted for electric current which would have a deflectable end portion performing the function of cutting tip 31 by inward and outward deflection, according to movement of 31 by lever 30 and linkage 29.

Figures 8, 9, 10:
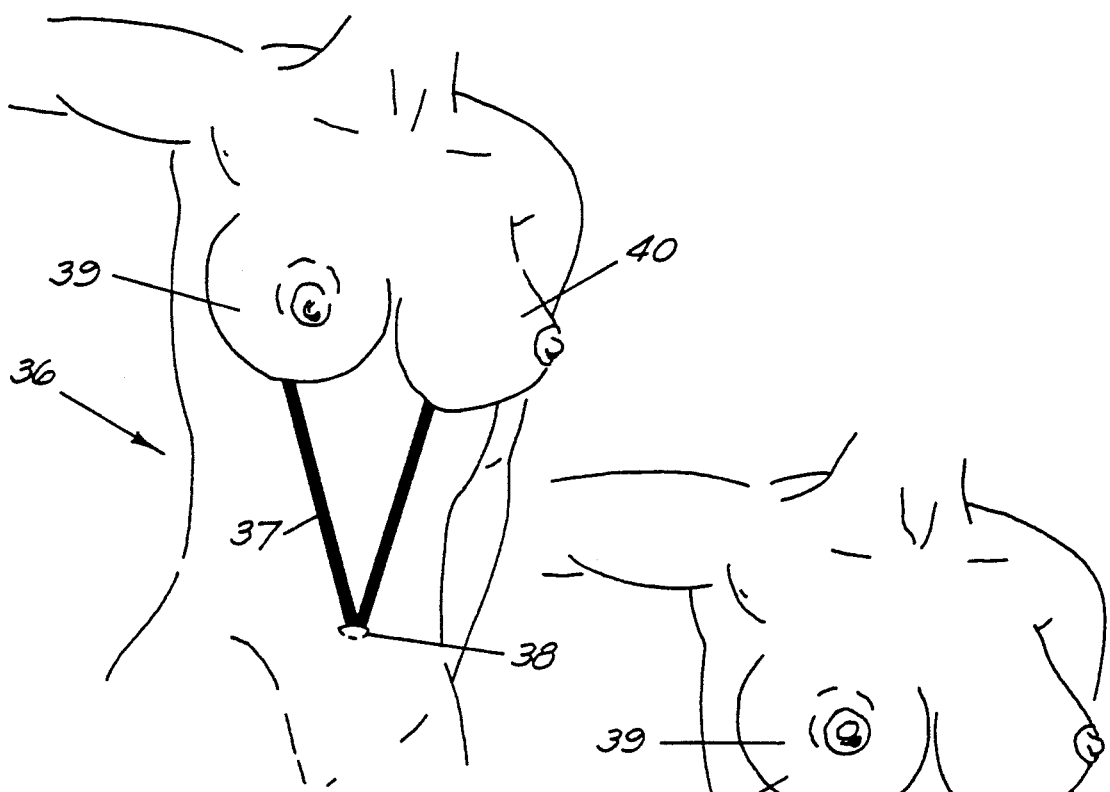
FIG. 8 is a plan view of a dissector used in separating tissue in the endoscopic breast augmentation mammoplasty according to a preferred embodiment of this invention.
FIG. 9 is a schematic view of a female torso with markings from the navel to the breasts for guidance of the surgeon in carrying out an endoscopic breast augmentation mammoplasty and a navel incision made according to a preferred embodiment of this invention.
FIG. 10 is a schematic view of a female torso, as in FIG. 9, with markings from the navel to the breasts for guidance of the surgeon in carrying out an endoscopic breast augmentation mammoplasty and showing the endotube and obturator of FIG. 1 partially inserted toward the right breast according to a preferred embodiment of this invention.

In FIG. 8, there is shown a dissector 32 for blunt dissection of tissue in the procedure described below. Dissector 32 has a handle 33 at one end and bent portion 34 at the other end. Bent portion 34 has a plurality of grooves 35 cut therein with sharp edges to facilitate dissection during the surgical procedure.

SURGICAL PROCEDURE FOR ENDOSCOPIC BREAST AUGMENTATION MAMMOPLASTY

This surgical procedure is a totally new and innovative combination of techniques for augmentation of the female breast. All procedures (shown in FIGS. 9-17) were performed under general anesthesia A female patient 36 is placed o the operating table and marks 37 made extending from the navel 38 to right breast 39 and left breast 40 in preparation for surgery (FIG. 9). An incision is made inside the navel 38 to commence the surgical procedure.

Endotube 14 and obturator 10 with a bullet shaped nose 13 (assembled as in FIG. 1) is introduced (FIG. 10) into this incision and is passed from the umbilicus, staying just above the fascia of the interior abdominal and chest wall, and below the subcutaneous tissue and fat, to a position just medial to the nipple and 6 to 8 centimeters above the level of the nipple. This movement produces a tunnel 41 leading to breast 39 and a space 42 behind the breast which is ultimately expanded into a pocket for a breast prosthesis or implant.

Figure 11:
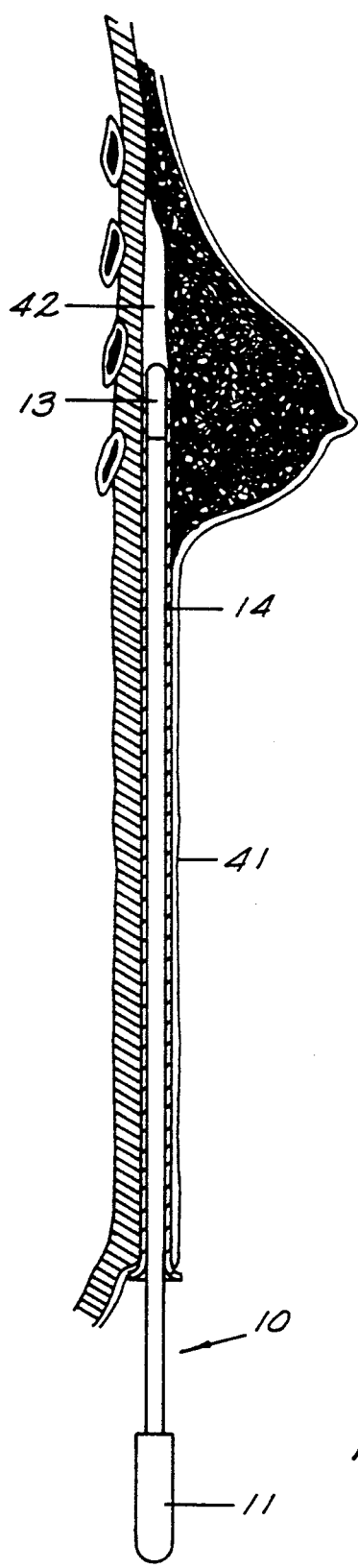
FIG. 11 is a sectional view of a female torso, including the rib cage and the breast between the breast tissue and muscle showing the endotube and obturator of FIG. 1 inserted beneath the breast to form a pocket to receive a prosthesis according to a preferred embodiment of this invention.
Figure 12:
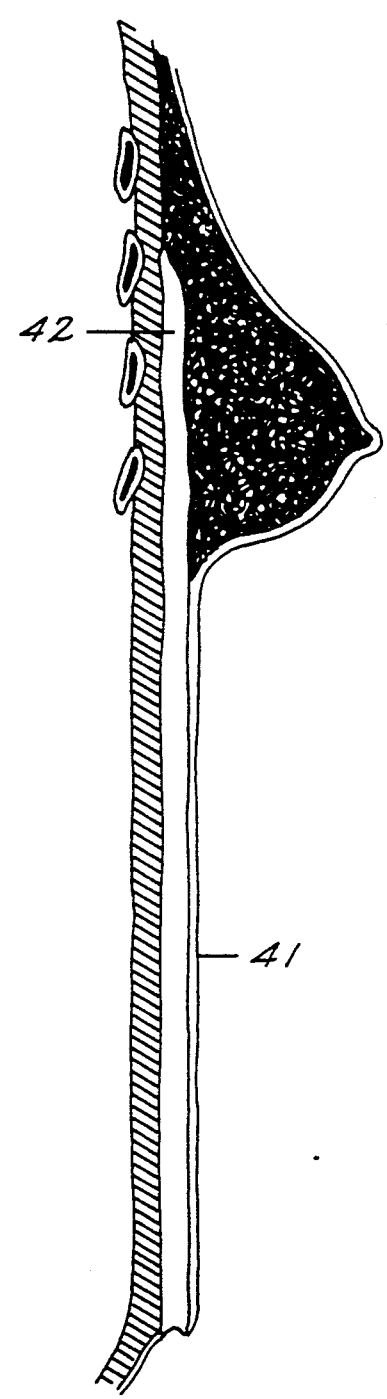
FIG. 12 is a sectional view of a female torso, including the rib cage and the breast, as in FIG. 11, showing the endotube and obturator removed to form a pocket to receive a prosthesis and a tunnel for insertion thereof according to a preferred embodiment of this invention.

As the endotube 10 (and obturator 14) is pushed over the inferior margin of the rib cage the operator manipulates the tube 14 with one hand and the breast with the other hand to keep the tube 14 below the breast tissue, but above the pectoralis muscle fascia, if the operator wishes to place the implant in the subglandular or submammary position. If the operator wishes to place the implant submuscular then the endotube 14 and breast are manipulated in order to allow penetration of the pectoralis muscle fibers and direct the endotube to a submuscular position. The formation of the tunnel 41 and space 42 are as shown in FIGS. 11 and 12.

The obturator 10 is then removed and the endoscope is introduced to verify position of the tunnel 41 and to inspect for bleeding. If bleeding is encountered or if further cutting or cauterization or cutting is required, the instrument 16 is introduced through endotube 14 and the cutting or cauterization carried out by blade 29 and cutting tip 31. The space or cavity 42 is irrigated through fitting 22 and passage 20 The cavity 42 is Whatever the final volume of the implant is intended to be, it is overfilled by a volume that is 50% greater than the intended final volume (FIG. 15). As the implant is being inflated and overexpanded the surgeon holds pressure and releases pressure in the appropriate manner to shape and form the pocket from space 42 as it is being created by the inflation/expansion of the implant.

The same procedure is done for the opposite breast 40.

Attention is turned back to the first breast 39 and the 50% "over-inflation" volume is removed. The fill tube 44 is removed by pulling it out from valve 45. Any FDA approved mammary implant having the desired structure may be used. One such implant that has proven satisfactory is the RTV SALINE-FILLED MAMMARY IMPLANT manufactured by McGhan Medical Corporation.

The same procedure is repeated for the opposite breast.

Using the endoscope, both breasts 39 and 40 are then inspected to be certain there is no pooling of saline to indicate a problem with a prosthesis and there is no excessive bleeding.

A "Y" tipped dissector (not shown) may be used to release any muscular or fibrous bands in the upper part of the breast pocket 42 that could not be released by expansion of the prosthesis or manipulations by the surgeon. A "hockey stick" dissector 32 may be used to release muscular or fibrous bands in the lower portion of the breast pocket 42. aspirated by suction applied through fitting 23, passage 21 and tip 24.

The endoscope and endotube 14 are then both withdrawn. An inflatable prosthesis or implant 43 (FIGS. 13 and 15-17) is completely evacuated of air and rolled up tightly. If the fill tube 44 on the implant 43 is considered to be in the 6 o'clock position, and the implant 43 is positioned so the valve 45 is on the underside. From the 3 o'clock position the implant is rolled up to the midline, then from the 9 o'clock position the other half of the implant is rolled up to the midline.

Figure 13:
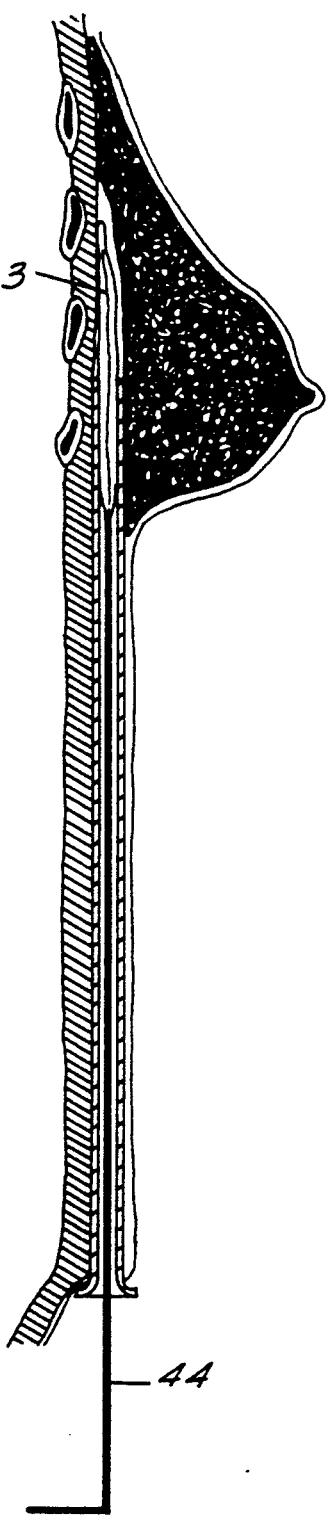
FIG. 13 is a sectional view of a female torso, including the rib cage and the breast showing the endotube and a breast prosthesis carried thereon inserted beneath the breast in the pocket formed in a previous step in the procedure and showing the prosthesis fill tube extending from the end of the endotube.

With the implant 43 tightly rolled in this fashion, the fill tube 44 of the implant is then passed through the endotube 14 from the front end of the endotube, coming out the back end. The implant 43 is then partially introduced into the end of the endotube 14 (FIG. 13).

At this point, the implant 43 is introduced into the tunnel 41 initially formed by the endotube 14 and is pushed through tunnel 41 to its position in space 42 beneath the breast, keeping the valve 45 of the implant 43 down (against the muscle). The implant 43 is held manually by the operator by squeezing the breast and the endotube 14 is then withdrawn to leave the implant in place with the fill tube 44 coming out through tunnel 41. Fill tube 44 of the implant 43 is connected to a syringe or other device 46 (FIG. 14) that fills the implant with sterile physiologic saline.

Both the "Y" tipped and "hockey stick" dissector 32 provide methods of blind-blunt dissection. The instrument 16 comprising an electrocautery endopod or a laser endopod, each containing a suction tube, irrigation tube and a small caliber endoscope plus the flexible or movable electrocautery tip or fiber optic laser tip may be used for sharp dissection under direct vision or coagulation of a bleeding vessel under direct vision.

At the conclusion of the procedure, the umbilical incision 38 is then sutured and a cotton ball put in place and taped and a bandage applied to the breast. The patient can go home directly from the recovery room without requiring hospitalization.

Advantages of this procedure over prior and current surgical procedures for breast augmentation are:

1. Only one incision is required to operate on both breasts.

2. The resultant scar is not on the breasts or in the axillary (arm pit) area, and is virtually invisible down inside the umbilicus.

3. There is minimal bleeding, bruising and swelling as a result of the "tissue expansion" technique to form the pocket, as opposed to the sharp and/or blunt techniques of dissection presently used.

4. There is much less damage to nerves than is caused by other techniques currently used.

The results of this new and improved endoscopic breast augmentation mammoplasty were evaluated on the basis of twenty cases during November-December 1991.

While this invention has been described fully and completely, it should be understood that, within the scope of the appended claims, the invention may be practiced otherwise than as specifically described.

We claim:

1. A method of endoscopic surgery for breast augmentation mammoplasty of a human patient comprising utilizing endoscopic instruments to perform the steps of
   making an incision at the navel of said patient,
   forming a tunnel in said patient underneath the skin and above the fascia from said incision to a point behind one breast, then
   providing an inflatable hollow prosthetic implant having an elongated filling tube, and inserting said implant through said incision and said tunnel to said point behind said breast,
   enlarging said point behind said breast into a pocket in which said implant is positioned,
   filling said implant with saline solution to a selected volume,
   removing said filling tube and closing said implant, and
   suturing or closing said navel incision.

2. A surgical method according to claim 1 including the step of manipulating said breast during filling to enlarge the point behind said breast into said pocket.

3. A surgical method according to claim 1 including repeating each of the steps above to augment a second breast.

4. A surgical method according to claim 1 including
   providing an endotube and an obturator having a bullet-shaped nose piece,
   placing said obturator inside said endotube with said nose piece protruding from a distal end of said endotube;
   inserting said endotube and protruding obturator nose piece through said incision and forcing them underneath the skin and above the fascia to form said tunnel extending to said point behind said breast where said pocket is formed,
   removing said endotube and obturator from said tunnel,
   rolling said implant compactly and placing the same at least partially inside the distal end of said endotube with said filling tube extending out a proximal end thereof,
   forcing said rolled implant and endotube through said tunnel to said pocket behind said breast,
   holding said implant in said pocket and removing said endotube from said tunnel,
   removing said filling tube after filling said implant, closing said implant, and
   suturing or closing said navel incision.

5. A surgical method according to claim 4 including the step of manipulating said breast during filling of said implant to enlarge said point behind said breast into said pocket.

6. A surgical method according to claim 4 including the step of
   marking the skin of said patient from the navel to each breast to identify the path of said endotube and obturator in forming said tunnel.

7. A surgical method according to claim 4 which includes
   removing said obturator from said endotube after formation of said tunnel and inserting an endoscope,
   viewing the interior of said tunnel and space behind said breast, and
   moving said endotube, as needed, to adjust the position of said tunnel.

8. A surgical method according to claim 4 in which
   said implant is overfilled with saline solution by a predetermined amount,
   said breast is manually manipulated during filling to open a pocket behind said breast, and
   said implant is subsequently relieved of a predetermined amount of overfill of liquid before removing said filling tube.

9. A surgical method according to claim 8 in which said implant is overfilled with saline solution by about 50% of a final volume.

10. A surgical method according to claim 8 in which
    said implant is overfilled with saline solution by a predetermined amount,
    said breast is manually manipulated during filling to open a pocket behind said breast,
    a blunt dissector is used in further opening said pocket behind said breast by releasing muscular or fibrous bands which were not released during overfilling of said implant and manipulation of said breast, and
    said implant is subsequently relieved of the amount of overfill of liquid before removing said filling tube.

11. A surgical method according to claim 10 in which
    said blunt dissector used in an upper portion of the breast pocket has a Y-shaped tip, and
    said blunt dissector used in a lower portion of the breast pocket is a rod with a right angled bent tip having longitudinal grooves spaced around the tip.

12. A surgical method according to claim 8 including the steps of
    providing a combined instrument for irrigation, application of vacuum, electrocutting and electro-cauterization, and endoscopic viewing constructed to fit said endotube,
    removing said obturator from said endotube after formation of said tunnel and inserting said combined instrument,
    viewing the interior of said tunnel and space behind said breast,
    moving said endotube, as needed, to adjust the position of said tunnel, and
    using said combined instrument, as needed, for cutting, cauterization and irrigation of said tunnel and space behind said breast.

13. A surgical method according to claim 8 including the steps of
    providing a combined instrument having a handle and a cylindrical body portion constructed to fit said endotube and having passages for irrigation, application of vacuum, electrocutting and electrocauterization, and endoscopic viewing,
    removing said obturator from said endotube after formation of said tunnel and inserting said combined instrument,
    viewing the interior of said tunnel and space behind said breast,
    moving said endotube, as needed, to adjust the position of said tunnel, and
    using said combined instrument, as needed, for cutting, cauterization and irrigation of said tunnel and space behind said breast.

14. A surgical method according to claim 8 including the steps of
    providing a combined instrument having a handle and a cylindrical boy portion constructed to fit said endotube and having pair of passages for separate irrigation and application of vacuum, a passage containing electrocutting and electrocauterization blade, and a passage sized to receive endoscope for viewing said tunnel and space behind said breast, removing said obturator from said endotube after formation of said tunnel and inserting said combined instrument, viewing the interior of said tunnel and space behind said breast, moving said endotube, as needed, to adjust the position of said tunnel, and using said combined instrument, as needed, for cutting, cauterization and irrigation of said tunnel and space behind said breast.

15. A surgical method according to claim 8 including the steps of providing a combined instrument having a handle and a cylindrical body portion constructed to fit said endotube and having pair of passages for separate irrigation and application of vacuum including an extensible nozzle for application of vacuum at a selected site, a passage containing electrocutting and electrocauterization blade and actuating means to move said blade angularly for cutting and cauterization a selected radial distance from said passage, and a passage sized to receive an endoscope for viewing said tunnel and space behind said breast, removing said obturator from said endotube after formation of said tunnel and inserting said combined instrument, viewing the interior of said tunnel and space behind said breast, moving said endotube, as needed, to adjust the position of said tunnel, and using said combined instrument, as needed, for cutting, cauterization and irrigation of said tunnel and space behind said breast.

16. A surgical method according to claim 8 including the steps of overfilling said implant with saline solution by a predetermined amount, manually manipulating said breast during filling to open a pocket behind said breast, using a blunt dissector in further opening said pocket behind said breast by releasing muscular or fibrous bands which were not released during overfilling of said implant and manipulation of said breast by the surgeon, and subsequently relieving said implant of the amount of overfill of liquid before removing said filling tube, providing a combined instrument for irrigation, application of vacuum, electrocutting and electro-cauterization, and endoscopic viewing constructed to fit said endotube, removing said obturator from said endotube after formation of said tunnel and inserting said combined instrument, viewing the interior of said tunnel and space behind said breast, moving said endotube, as needed, to adjust the position of said tunnel, and using said combined instrument, as needed, for cutting, cauterization and irrigation of said tunnel and space behind said breast.

17. A surgical method according to claim 8 including the steps of overfilling said implant with saline solution by a predetermined amount, manually manipulating said breast during filling to open a pocket behind said breast, using a blunt dissector in further opening said pocket behind said breast by releasing muscular or fibrous bands which were not released during overfilling of said implant and manipulation of said breast, and subsequently relieving said implant of a predetermined amount of overfill of liquid and then removing said filling tube, providing a combined instrument having a handle and a cylindrical body portion constructed to fit said endotube and having passages for irrigation, application of vacuum, electrocutting and electrocauterization, and endoscopic viewing, removing said obturator from said endotube after formation of said tunnel and inserting said combined instrument, viewing the interior of said tunnel and space behind said breast, moving said endotube, as needed, to adjust the position of said tunnel, and using said combined instrument, as needed, for cutting, cauterization and irrigation of said tunnel and space behind said breast.

18. A surgical method according to claim 8 including the steps of overfilling said implant with saline solution by a predetermined amount, manually manipulating said breast during filling to open a pocket behind said breast, using a blunt dissector in further opening said pocket behind said breast by releasing muscular or fibrous bands which were not released during overfilling of said implant and manipulation of said breast, and subsequently relieving said implant of the amount of overfill of liquid before removing said filling tube, providing a combined instrument having a handle and a cylindrical body portion constructed to fit said endotube and having a pair of passages for separate irrigation and application of vacuum, a passage containing an electrocutting and electrocauterization blade, and a passage sized to receive endoscope for viewing said tunnel and space behind said breast, removing said obturator from said endotube after formation of said tunnel and inserting said combined instrument, viewing the interior of said tunnel and space behind said breast, moving said endotube, as needed, to adjust the position of said tunnel, and using said combined instrument, as needed, for cutting, cauterization and irrigation of said tunnel and space behind said breast.

19. A surgical method according to claim 8 including the steps of overfilling said implant with saline solution by a predetermined amount, manually manipulating said breast during filling to open a pocket behind said breast, using a blunt dissector in further opening said pocket behind said breast by releasing muscular or fibrous bands which were not released during overfilling of said implant and manipulation of said breast by the surgeon, and subsequently relieving said implant of a predetermined amount of overfill of liquid before removing said filling tube, providing a combined instrument having a handle and a cylindrical body portion constructed to fit said endotube and having pair of passages for separate irrigation and application of vacuum including an extensible nozzle for application of vacuum at a selected site, a passage containing an electrocutting and electrocauterization blade and actuating means to move said blade angularly for cutting and cauterization a selected radial distance from said passage, and a passage sized to receive endoscope for viewing said tunnel and space behind said breast, removing said obturator from said endotube after formation of said tunnel and inserting said combined instrument, viewing the interior of said tunnel and space behind said breast, moving said endotube, as needed, to adjust the position of said tunnel, and using said combined instrument, as needed, for cutting, cauterization and irrigation of said tunnel and space behind said breast.

20. A surgical method according to claim 8 including marking said patient from the navel to each breast to identify the path of the tunnel formed by said endotube and obturator, overfilling said implant with saline solution by about 50% of the final volume, manually manipulating said breast during filling to open a pocket behind said breast, using a blunt dissector in further opening said pocket behind said breast by releasing muscular or fibrous bands which have not released during overfilling of said implant and manipulation of said breast, subsequently relieving said implant of the amount of overfill of liquid before removing said filling tube, providing a combined instrument having a handle and a cylindrical body portion constructed to fit said endotube and having pair of passages for separate irrigation and application of vacuum, a passage containing an electrocutting and electrocauterization blade, and a passage sized to receive an endoscope for viewing said tunnel and space behind said breast, removing said obturator from said endotube after formation of said tunnel and inserting said combined instrument, viewing the interior of said tunnel and space behind said breast, moving said endotube, as needed, to adjust the position of said tunnel, using said combined instrument, as needed, for cutting, cauterization and irrigation of said tunnel and space behind said breast, and repeating all of the above steps to augment a second breast.

* * * * *